United States Patent
Plöger et al.

(10) Patent No.: US 9,718,867 B2
(45) Date of Patent: Aug. 1, 2017

(54) GDF-5 MUTANT FOR INDUCING CARTILAGE FORMATION

(71) Applicant: BIOPHARM GESELLSCHAFT ZUR BIOTECHNOLOGISCHEN ENTWICKLUNG VON PHARMAKA MBH, Heidelberg (DE)

(72) Inventors: Frank Plöger, Heidelberg (DE); Florian Wagner, Heidelberg (DE)

(73) Assignee: BIOPHARMA GESELLSCHAFT ZUR BIOTECHNOLOGISCHEN ENTWICKLUNG VON PHARMAKA MBH, Heidelberg (DE)

( * ) Notice: Subject to any disclaimer, the term of this patent is extended or adjusted under 35 U.S.C. 154(b) by 0 days.

(21) Appl. No.: 14/362,691

(22) PCT Filed: Dec. 5, 2012

(86) PCT No.: PCT/EP2012/074549
§ 371 (c)(1),
(2) Date: Jun. 4, 2014

(87) PCT Pub. No.: WO2013/083649
PCT Pub. Date: Jun. 13, 2013

(65) Prior Publication Data
US 2014/0369978 A1 Dec. 18, 2014

(30) Foreign Application Priority Data
Dec. 5, 2011 (EP) ..................................... 11191973

(51) Int. Cl.
*C07K 14/51* (2006.01)
*C07K 14/495* (2006.01)

(52) U.S. Cl.
CPC ............ *C07K 14/495* (2013.01); *C07K 14/51* (2013.01)

(58) Field of Classification Search
None
See application file for complete search history.

(56) References Cited

U.S. PATENT DOCUMENTS

| 5,801,014 A | 9/1998 | Lee et al. | |
| 8,188,226 B2 * | 5/2012 | Pohl | C07K 14/495 424/423 |

FOREIGN PATENT DOCUMENTS

| EP | 1698691 | 9/2006 |
| EP | 1721909 | 11/2006 |
| JP | 2007502108 A | 2/2007 |
| JP | 2007054013 A | 3/2007 |
| JP | 2009533020 A | 9/2009 |
| WO | 9504819 | 2/1995 |
| WO | 9614335 | 5/1996 |
| WO | 9633215 | 10/1996 |
| WO | 9704095 | 2/1997 |
| WO | 9706254 | 2/1997 |
| WO | 9821972 | 5/1998 |
| WO | 9961611 | 12/1999 |
| WO | 0021998 | 4/2000 |
| WO | 0111041 | 2/2001 |
| WO | 0192298 | 12/2001 |
| WO | 2005014821 A1 | 2/2005 |
| WO | 2005085281 | 9/2005 |
| WO | 2006094722 | 9/2006 |
| WO | 2007057212 | 5/2007 |
| WO | 2007110631 A1 | 10/2007 |
| WO | 2008049588 | 5/2008 |
| WO | 2012023113 | 2/2012 |

OTHER PUBLICATIONS

Byrnes et al., Mutations in GDF5 Presenting as Semidominant Brachydactyly A1. Human Mutation, vol. 31, No. 10, 1155-1162, 2010.*
Degenkolbe et al., A GDF5 Point Mutation Strikes Twice—Causing BDA1 and SYNS2. PLOS Genetics. Oct. 2013 | vol. 9 | Issue 10 | e1003846.*
NCBI, dbSNP rs748144622, Mar. 4, 2015, p. 1-2.*
NCBI, dbSNP rs756378924, Mar. 4, 2015, p. 1-2.*
NCBI, dbSNP rs770851716, Mar. 4, 2015, p. 1-2.*
Tokuriki et al., Stability effects of mutations and protein evolvability. Curr Opin Struct Biol. Oct. 2009;19(5):596-604.*
Alaoui-Ismaili et al., "Design of second generation therapeutic recombinant bone morphogenetic proteins", Cytokine & growth factor reviews 20.5 (2009): 501-507.
Kamiya et al., "New insights on the roles of BMP signaling in bone—A review of recent mouse genetic studies", Biofactors. Mar.-Apr. 2011; 37(2): 75-82.
Kasten et al., "The effect of two point mutations in GDF-5 on ectopic bone formation in a β-tricalciumphosphate scaffold", Biomaterials 31.14 (2010): 3878-3884.
Kotzsch et al., "Crystal structure analysis reveals a spring-loaded latch as molecular mechanism for GDF-5-type I receptor specificity", The EMBO journal 28.7 (2009): 937-947.
Masuya et al., "A novel dominant-negative mutation in Gdf5 generated by ENU mutagenesis impairs joint formation and causes osteoarthritis in mice", Human molecular genetics 16.19 (2007): 2366-2375.
Nakamura, Koji, et al. "p38 mitogen-activated protein kinase functionally contributes to chondrogenesis induced by growth/differentiation factor-5 in ATDC5 cells", Experimental cell research 250.2 (1999): 351-363. Abstract Only.
Nickel et al., "A single residue of GDF-5 defines binding specificity to BMP receptor IB", Journal of molecular biology 349.5 (2005): 933-947.

(Continued)

*Primary Examiner* — Scott Long
*Assistant Examiner* — Arthur S Leonard
(74) *Attorney, Agent, or Firm* — Kilpatrick Townsend & Stockton LLP

(57) ABSTRACT

The present invention is directed to GDF-5 related proteins having an improved capability of inducing cartilage formation and a reduced capability of inducing bone formation. The novel proteins are particularly useful in the treatment of cartilage defects, wherein the formation of bone tissue is undesirable.

12 Claims, 8 Drawing Sheets

(56) References Cited

OTHER PUBLICATIONS

International Application No. PCT/EP2012/074549, International Preliminary Report on Patentability dated Feb. 17, 2014.
International Application No. PCT/EP2012/074549, International Search Report dated Jan. 22, 2013.
International Application No. PCT/EP2012/074549, Swedish Novelty Search Report dated Apr. 2, 2012.
International Application No. PCT/EP2012/074549, Swedish Preliminary Patentability Opinion dated Apr. 5, 2014.
Schreuder et al., "Crystal structure of recombinant human growth and differentiation factor 5: evidence for interaction of the type I and type II receptor-binding sites", Biochemical and biophysical research communications 329.3 (2005): 1076-1086.
Seemann et al., "Activating and deactivating mutations in the receptor interaction site of GDF5 cause symphalangism or brachydactyly type A2", Journal of Clinical Investigation 115.9 (2005): 2373-2381.
Seemann et al., "Mutations in GDF5 reveal a key residue mediating BMP inhibition by NOGGIN", PLoS genetics, vol. 5, No. 11 (2009).
Takanashi, Hitoshi, et al., "Establishment and characterization of stromal cell lines that support differentiation of murine hematopoietic blast cells into osteoclast-like cells", In Vitro Cellular & Developmental Biology—Animal 30.6 (1994): 384-393. Abstract Only.
Baur et al., "Combinatorial signaling through BMP receptor IB and GDF5: shaping of the distal mouse limb and the genetics of distal limb diversity", Development 127.3 (2000): 605-619.
Chang et al., "Cartilage-derived morphogenetic proteins. New members of the transforming growth factor-beta superfamily predominantly expressed in long bones during human embryonic development", Journal of Biological Chemistry 269 45 (1994): 28227-28234.
Cheng et al., "Osteogenic activity of the fourteen types of human bone morphogenetic proteins (BMPs)", The journal of bone & joint surgery 85.8 (2003): 1544-1552.
Kirker-Head, "Potential applications and delivery strategies for bone morphogenetic proteins", Advanced drug delivery reviews 43.1 (2000): 65-92.
Massagué, "TGFβ signaling: receptors, transducers, and Mad proteins", Cell, vol. 85 (1996): 947-950.
Mishina et al., "Bmpr encodes a type I bone morphogenetic protein receptor that is essential for gastrulation during mouse embryogenesis", Genes & Dev. 1995. 9: 3027-3037.
Sanyal et al., "Isolation of a cDNA sequence of rabbit GDF5 (mature form) and pattern of its mRNA expression during periosteal chondrogenesis", Molecular biotechnology 16.3 (2000): 203-210.
Settle JR et al., "Multiple joint and skeletal patterning defects caused by single and double mutations in the mouse *Gdf6* and *Gdf5* genes", Developmental biology 254.1 (2003): 116-130.
Storm et al., "GDF5 coordinates bone and joint formation during digit development", Developmental biology 209.1 (1999): 11-27.
Storm et al., "Joint patterning defects caused by single and double mutations in members of the bone morphogenetic protein (BMP) family", Development 122.12 (1996): 3969-3979.
Storm et al., "Limb alterations in brachypodism mice due to mutations in a new member of the TGFb-superfamily", Nature 368.6472 (1994): 639-642.
Thomas et al., "Disruption of human limb morphogenesis by a dominant negative mutation in CDMP1", Nature genetics 17.1 (1997): 58-64.
Wolfman et al., "Ectopic induction of tendon and ligament in rats by growth and differentiation factors 5, 6, and 7, members of the TGF-beta gene family", Journal of Clinical Investigation 100.2 (1997): 321.
Zou et al., "Distinct roles of type I bone morphogenetic protein receptors in the formation and differentiation of cartilage", Genes & Dev. 1997. 11: 2191-2203.
Ebina K., et al. Biochemical and Biophysical Research Communications, 2009, vol. 378, pp. 186-191, 7 pages.
Japanese Application No. 2014543942, "Notification of Reason(s) for Refusal", mailed May 25, 2016.
English translation of Japanese Application No. 2014543942, "Notification of Reason(s) for Refusal", mailed May 25, 2016.

* cited by examiner

```
            1   mrlpklltfl   lwylawldle   fictvlgapd
lgqrpqgtrp glakaeaker pplarnvfrp 61   gghsygggat   nanarakggt   gqtggltqpk
kdepkklppr pggpepkpgh ppqtrqatar 121   tvtpkgqlpg   gkappkagsv   pssfllkkar
epgpprepke pfrpppitph eymlslyrtl 181   sdadrkggns   svkleaglan   titsfidkgq
ddrgpvvrkq ryvfdisale kdgllgaelr 241   ilrkkpsdta   kpaapgggra   aqlklsscps
grqpaslldv rsvpgldgsg wevfdiwklf 301   rnfknsaqlc   leleawergr   avdlrglgfd
raarqvheka lflvfgrtkk rdlffneika 361   rsgqddktvy   eylfsqrrkr   raplatrqgk
rpsknlkarc srkalhvnfk dmqwddwiia 421   pleyeafhce   glcefplrsh   leptnhaviq
tlmnsmdpes tpptccvptr lspisilfid 481 sannvvykqy edmvvescqc r
```

FIG. 1

Fig. 8
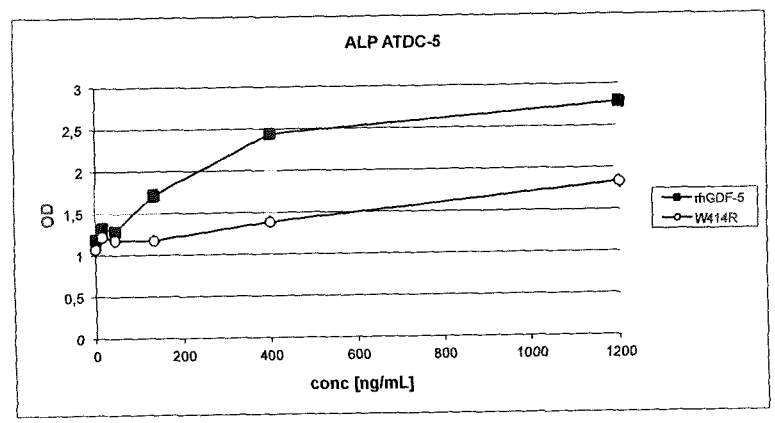
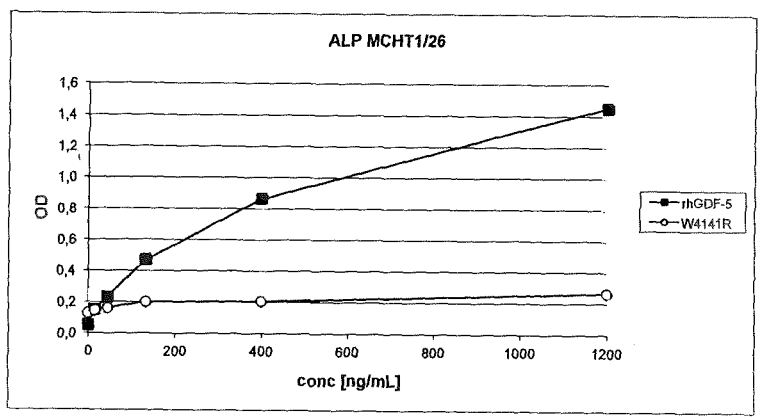

SEQUENCE LISTING

<160> NUMBER OF SEQ ID NOS: 6

<210> SEQ ID NO 1
<211> LENGTH: 2703
<212> TYPE: DNA
<213> ORGANISM: homo sapiens
<220> FEATURE:
<221> NAME/KEY: CDS
<222> LOCATION: (640)..(2142)
<223> OTHER INFORMATION: GDF-5 precursor

<400> SEQUENCE: 1

```
ccatggcctc gaaagggcag cggtgatttt tttcacataa atatatcgca cttaaatgag      60
tttagacagc atgacatcag agagtaatta aattggtttg ggttggaatt ccgtttccaa     120
ttcctgagtt caggtttgta aaagattttt ctgagcacct gcaggcctgt gagtgtgtgt     180
gtgtgtgtgt gtgtgtgtgt gtgtgtgtga agtattttca ctggaaagga ttcaaaacta     240
gggggaaaaa aaaactggag cacacaggca gcattacgcc attcttcctt cttggaaaaa     300
tccctcagcc ttatacaagc ctccttcaag ccctcagtca gttgtgcagg agaaagggg     360 cggttggctt tctcctttca agaacgagtt attttcagct gctgactgga gacggtgcac     420
gtctggatac gagagcattt ccactatggg actggataca aacacacacc cggcagactt     480
caagagtctc agactgagga gaaagccttt ccttctgctg ctactgctgc tgccgctgct     540
tttgaaagtc cactccttc atggttttc ctgccaaacc agaggcacct ttgctgctgc      600
cgctgttctc tttggtgtca ttcagcggct ggccagagg atg aga ctc ccc aaa       654
                                               Met Arg Leu Pro Lys
                                                 1               5 ctc ctc act ttc ttg ctt tgg tac ctg gct tgg ctg gac ctg gaa ttc      702
Leu Leu Thr Phe Leu Leu Trp Tyr Leu Ala Trp Leu Asp Leu Glu Phe
```

```
                        10                      15                      20
atc tgc act gtg ttg ggt gcc cct gac ttg ggc cag aga ccc cag ggg        750
Ile Cys Thr Val Leu Gly Ala Pro Asp Leu Gly Gln Arg Pro Gln Gly
            25                      30                      35 acc agg cca gga ttg gcc aaa gca gag gcc aag gag agg ccc ccc ctg        798
Thr Arg Pro Gly Leu Ala Lys Ala Glu Ala Lys Glu Arg Pro Pro Leu
        40                      45                      50 gcc cgg aac gtc ttc agg cca ggg ggt cac agc tat ggt ggg ggg gcc        846
Ala Arg Asn Val Phe Arg Pro Gly Gly His Ser Tyr Gly Gly Gly Ala
    55                      60                      65 acc aat gcc aat gcc agg gca aag gga ggc acc ggg cag aca gga ggc        894
Thr Asn Ala Asn Ala Arg Ala Lys Gly Gly Thr Gly Gln Thr Gly Gly
70                      75                      80                      85 ctg aca cag ccc aag aag gat gaa ccc aaa aag ctg ccc ccc aga ccg        942
Leu Thr Gln Pro Lys Lys Asp Glu Pro Lys Lys Leu Pro Pro Arg Pro
                    90                      95                      100 ggc ggc cct gaa ccc aag cca gga cac cct ccc caa aca agg cag gct        990
Gly Gly Pro Glu Pro Lys Pro Gly His Pro Pro Gln Thr Arg Gln Ala
                105                     110                     115 aca gcc cgg act gtg acc cca aaa gga cag ctt ccc gga ggc aag gca       1038
Thr Ala Arg Thr Val Thr Pro Lys Gly Gln Leu Pro Gly Gly Lys Ala
            120                     125                     130 ccc cca aaa gca gga tct gtc ccc agc tcc ttc ctg ctg aag aag gcc       1086
Pro Pro Lys Ala Gly Ser Val Pro Ser Ser Phe Leu Leu Lys Lys Ala
        135                     140                     145 agg gag ccc ggg ccc cca cga gag ccc aag gag ccg ttt cgc cca ccc       1134
Arg Glu Pro Gly Pro Pro Arg Glu Pro Lys Glu Pro Phe Arg Pro Pro
150                     155                     160                     165 ccc atc aca ccc cac gag tac atg ctc tcg ctg tac agg acg ctg tcc       1182
Pro Ile Thr Pro His Glu Tyr Met Leu Ser Leu Tyr Arg Thr Leu Ser
                    170                     175                     180 gat gct gac aga aag gga ggc aac agc agc gtg aag ttg gag gct ggc       1230
Asp Ala Asp Arg Lys Gly Gly Asn Ser Ser Val Lys Leu Glu Ala Gly
                185                     190                     195 ctg gcc aac acc atc acc agc ttt att gac aaa ggg caa gat gac cga       1278
Leu Ala Asn Thr Ile Thr Ser Phe Ile Asp Lys Gly Gln Asp Asp Arg
            200                     205                     210 ggt ccc gtg gtc agg aag cag agg tac gtg ttt gac att agt gcc ctg       1326
Gly Pro Val Val Arg Lys Gln Arg Tyr Val Phe Asp Ile Ser Ala Leu
        215                     220                     225 gag aag gat ggg ctg ctg ggg gcc gag ctg cgg atc ttg cgg aag aag       1374
Glu Lys Asp Gly Leu Leu Gly Ala Glu Leu Arg Ile Leu Arg Lys Lys
230                     235                     240                     245 ccc tcg gac acg gcc aag cca gcg gcc ccc gga ggc ggg cgg gct gcc       1422
Pro Ser Asp Thr Ala Lys Pro Ala Ala Pro Gly Gly Gly Arg Ala Ala
                    250                     255                     260 cag ctg aag ctg tcc agc tgc ccc agc ggc cgg cag ccg gcc tcc ttg       1470
Gln Leu Lys Leu Ser Ser Cys Pro Ser Gly Arg Gln Pro Ala Ser Leu
                265                     270                     275 ctg gat gtg cgc tcc gtg cca ggc ctg gac gga tct ggc tgg gag gtg       1518
Leu Asp Val Arg Ser Val Pro Gly Leu Asp Gly Ser Gly Trp Glu Val
            280                     285                     290 ttc gac atc tgg aag ctc ttc cga aac ttt aag aac tcg gcc cag ctg       1566
Phe Asp Ile Trp Lys Leu Phe Arg Asn Phe Lys Asn Ser Ala Gln Leu
        295                     300                     305 tgc ctg gag ctg gag gcc tgg gaa cgg ggc agg gcc gtg gac ctc cgt       1614
Cys Leu Glu Leu Glu Ala Trp Glu Arg Gly Arg Ala Val Asp Leu Arg
310                     315                     320                     325 ggc ctg ggc ttc gac cgc gcc gcc cgg cag gtc cac gag aag gcc ctg       1662
```

-continued

| | | | | | | | | | | | | |
|---|---|---|---|---|---|---|---|---|---|---|---|---|
|Gly|Leu|Gly|Phe|Asp|Arg|Ala|Ala|Arg|Gln|Val|His|Glu|Lys|Ala|Leu|
| | | | |330| | | |335| | | |340| | | |

```
ttc ctg gtg ttt ggc cgc acc aag aaa cgg gac ctg ttc ttt aat gag    1710
Phe Leu Val Phe Gly Arg Thr Lys Lys Arg Asp Leu Phe Phe Asn Glu
            345                 350                 355 att aag gcc cgc tct ggc cag gac gat aag acc gtg tat gag tac ctg    1758
Ile Lys Ala Arg Ser Gly Gln Asp Asp Lys Thr Val Tyr Glu Tyr Leu
        360                 365                 370 ttc agc cag cgg cga aaa cgg cgg gcc cca ctg gcc act cgc cag ggc    1806
Phe Ser Gln Arg Arg Lys Arg Arg Ala Pro Leu Ala Thr Arg Gln Gly
    375                 380                 385 aag cga ccc agc aag aac ctt aag gct cgc tgc agt cgg aag gca ctg    1854
Lys Arg Pro Ser Lys Asn Leu Lys Ala Arg Cys Ser Arg Lys Ala Leu
390                 395                 400                 405 cat gtc aac ttc aag gac atg ggc tgg gac gac tgg atc atc gca ccc    1902
His Val Asn Phe Lys Asp Met Gly Trp Asp Asp Trp Ile Ile Ala Pro
            410                 415                 420 ctt gag tac gag gct ttc cac tgc gag ggg ctg tgc gag ttc cca ttg    1950
Leu Glu Tyr Glu Ala Phe His Cys Glu Gly Leu Cys Glu Phe Pro Leu
        425                 430                 435 cgc tcc cac ctg gag ccc acg aat cat gca gtc atc cag acc ctg atg    1998
Arg Ser His Leu Glu Pro Thr Asn His Ala Val Ile Gln Thr Leu Met
    440                 445                 450 aac tcc atg gac ccc gag tcc aca cca ccc acc tgc tgt gtg ccc acg    2046
Asn Ser Met Asp Pro Glu Ser Thr Pro Pro Thr Cys Cys Val Pro Thr
455                 460                 465 cgg ctg agt ccc atc agc atc ctc ttc att gac tct gcc aac aac gtg    2094
Arg Leu Ser Pro Ile Ser Ile Leu Phe Ile Asp Ser Ala Asn Asn Val
470                 475                 480                 485 gtg tat aag cag tat gag gac atg gtc gtg gag tcg tgt ggc tgc agg    2142
Val Tyr Lys Gln Tyr Glu Asp Met Val Val Glu Ser Cys Gly Cys Arg
            490                 495                 500 tagcagcact ggccctctgt cttcctgggt ggcacatccc aagagcccct tcctgcactc    2202
ctggaatcac agaggggtca ggaagctgtg gcaggagcat ctacacagct tgggtgaaag    2262
gggattccaa taagcttgct cgctctctga gtgtgacttg gctaaaggc cccctttttat    2322
ccacaagttc ccctggctga ggattgctgc cgtctgctg atgtgaccag tggcaggcac    2382
aggtccaggg agacagactc tgaatgggac tgagtcccag gaaacagtgc tttccgatga    2442
gactcagccc accatttctc ctcacctggg ccttctcagc ctctggactc tcctaagcac    2502
ctctcaggag agccacaggt gccactgcct cctcaaatca catttgtgcc tggtgacttc    2562
ctgtccctgg gacagttgag aagctgactg ggcaagagtg ggagagaaga ggagagggct    2622
tggatagagt tgaggagtgt gaggctgtta gactgttaga tttaaatgta tattgatgag    2682
ataaaaagca aaactgtgcc t                                              2703
```

<210> SEQ ID NO 2
<211> LENGTH: 501
<212> TYPE: PRT
<213> ORGANISM: homo sapiens

<400> SEQUENCE: 2

| | | | | | | | | | | | | | | | |
|---|---|---|---|---|---|---|---|---|---|---|---|---|---|---|---|
|Met|Arg|Leu|Pro|Lys|Leu|Leu|Thr|Phe|Leu|Leu|Trp|Tyr|Leu|Ala|Trp|
|1| | | |5| | | | |10| | | | |15| |

| | | | | | | | | | | | | |
|---|---|---|---|---|---|---|---|---|---|---|---|---|---|---|---|
|Leu|Asp|Leu|Glu|Phe|Ile|Cys|Thr|Val|Leu|Gly|Ala|Pro|Asp|Leu|Gly|
| | | |20| | | | |25| | | | |30| | |

| | | | | | | | | | | | | |
|---|---|---|---|---|---|---|---|---|---|---|---|---|---|---|---|
|Gln|Arg|Pro|Gln|Gly|Thr|Arg|Pro|Gly|Leu|Ala|Lys|Ala|Glu|Ala|Lys|
| | |35| | | | |40| | | | |45| | | |

```
Glu Arg Pro Pro Leu Ala Arg Asn Val Phe Arg Pro Gly Gly His Ser
     50                  55                  60

Tyr Gly Gly Gly Ala Thr Asn Ala Asn Ala Arg Ala Lys Gly Gly Thr
 65                  70                  75                  80

Gly Gln Thr Gly Gly Leu Thr Gln Pro Lys Lys Asp Glu Pro Lys Lys
                 85                  90                  95

Leu Pro Pro Arg Pro Gly Gly Pro Glu Pro Lys Pro Gly His Pro Pro
             100                 105                 110

Gln Thr Arg Gln Ala Thr Ala Arg Thr Val Thr Pro Lys Gly Gln Leu
         115                 120                 125

Pro Gly Gly Lys Ala Pro Pro Lys Ala Gly Ser Val Pro Ser Ser Phe
     130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                 165                 170                 175

Tyr Arg Thr Leu Ser Asp Ala Asp Arg Lys Gly Gly Asn Ser Ser Val
             180                 185                 190

Lys Leu Glu Ala Gly Leu Ala Asn Thr Ile Thr Ser Phe Ile Asp Lys
         195                 200                 205

Gly Gln Asp Asp Arg Gly Pro Val Val Arg Lys Gln Arg Tyr Val Phe
     210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Ala Pro Gly
                 245                 250                 255

Gly Gly Arg Ala Ala Gln Leu Lys Leu Ser Ser Cys Pro Ser Gly Arg
             260                 265                 270

Gln Pro Ala Ser Leu Leu Asp Val Arg Ser Val Pro Gly Leu Asp Gly
         275                 280                 285

Ser Gly Trp Glu Val Phe Asp Ile Trp Lys Leu Phe Arg Asn Phe Lys
     290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                 325                 330                 335

His Glu Lys Ala Leu Phe Leu Val Phe Gly Arg Thr Lys Lys Arg Asp
             340                 345                 350

Leu Phe Phe Asn Glu Ile Lys Ala Arg Ser Gly Gln Asp Asp Lys Thr
     355                 360                 365

Val Tyr Glu Tyr Leu Phe Ser Gln Arg Arg Lys Arg Arg Ala Pro Leu
 370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                 405                 410                 415

Trp Ile Ile Ala Pro Leu Glu Tyr Glu Ala Phe His Cys Glu Gly Leu
             420                 425                 430

Cys Glu Phe Pro Leu Arg Ser His Leu Glu Pro Thr Asn His Ala Val
         435                 440                 445

Ile Gln Thr Leu Met Asn Ser Met Asp Pro Glu Ser Thr Pro Pro Thr
     450                 455                 460
```

```
Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
            485                 490                 495

Ser Cys Gly Cys Arg
            500

<210> SEQ ID NO 3
<211> LENGTH: 360
<212> TYPE: DNA
<213> ORGANISM: Homo sapiens
<220> FEATURE:
<221> NAME/KEY: CDS
<222> LOCATION: (1)..(360)
<223> OTHER INFORMATION: human mature monomeric GDF-5

<400> SEQUENCE: 3 gca cca cta gca act cgt cag ggc aag cga ccc agc aag aac ctt aag      48
Ala Pro Leu Ala Thr Arg Gln Gly Lys Arg Pro Ser Lys Asn Leu Lys
1               5                   10                  15 gct cgc tgc agt cgg aag gca ctg cat gtc aac ttc aag gac atg ggc      96
Ala Arg Cys Ser Arg Lys Ala Leu His Val Asn Phe Lys Asp Met Gly
            20                  25                  30 tgg gac gac tgg atc atc gca ccc ctt gag tac gag gct ttc cac tgc     144
Trp Asp Asp Trp Ile Ile Ala Pro Leu Glu Tyr Glu Ala Phe His Cys
        35                  40                  45 gag ggg ctg tgc gag ttc cca ttg cgc tcc cac ctg gag ccc acg aat     192
Glu Gly Leu Cys Glu Phe Pro Leu Arg Ser His Leu Glu Pro Thr Asn
50                  55                  60 cat gca gtc atc cag acc ctg atg aac tcc atg gac ccc gag tcc aca     240
His Ala Val Ile Gln Thr Leu Met Asn Ser Met Asp Pro Glu Ser Thr
65                  70                  75                  80 cca ccc acc gcc tgt gtg ccc acg cga ctg agt ccc atc agc atc ctc     288
Pro Pro Thr Ala Cys Val Pro Thr Arg Leu Ser Pro Ile Ser Ile Leu
                85                  90                  95 ttc att gac tct gcc aac aac gtg gtg tat aag cag tat gag gac atg     336
Phe Ile Asp Ser Ala Asn Asn Val Val Tyr Lys Gln Tyr Glu Asp Met
            100                 105                 110 gtc gtg gag tcg tgt ggc tgt agg                                     360
Val Val Glu Ser Cys Gly Cys Arg
        115                 120

<210> SEQ ID NO 4
<211> LENGTH: 120
<212> TYPE: PRT
<213> ORGANISM: Homo sapiens

<400> SEQUENCE: 4

Ala Pro Leu Ala Thr Arg Gln Gly Lys Arg Pro Ser Lys Asn Leu Lys
1               5                   10                  15

Ala Arg Cys Ser Arg Lys Ala Leu His Val Asn Phe Lys Asp Met Gly
            20                  25                  30

Trp Asp Asp Trp Ile Ile Ala Pro Leu Glu Tyr Glu Ala Phe His Cys
        35                  40                  45

Glu Gly Leu Cys Glu Phe Pro Leu Arg Ser His Leu Glu Pro Thr Asn
50                  55                  60

His Ala Val Ile Gln Thr Leu Met Asn Ser Met Asp Pro Glu Ser Thr
65                  70                  75                  80

Pro Pro Thr Ala Cys Val Pro Thr Arg Leu Ser Pro Ile Ser Ile Leu
                85                  90                  95
```

```
Phe Ile Asp Ser Ala Asn Asn Val Val Tyr Lys Gln Tyr Glu Asp Met
            100                 105                 110

Val Val Glu Ser Cys Gly Cys Arg
        115                 120

<210> SEQ ID NO 5
<211> LENGTH: 102
<212> TYPE: PRT
<213> ORGANISM: Homo sapiens
<220> FEATURE:
<221> NAME/KEY: DOMAIN
<222> LOCATION: (1)..(102)
<223> OTHER INFORMATION: cystine-knot domain of GDF-6

<400> SEQUENCE: 5

Cys Ser Lys Lys Pro Leu His Val Asn Phe Lys Glu Leu Gly Trp Asp
1               5                   10                  15

Asp Trp Ile Ile Ala Pro Leu Glu Tyr Glu Ala Tyr His Cys Glu Gly
            20                  25                  30

Val Cys Asp Phe Pro Leu Arg Ser His Leu Glu Pro Thr Asn His Ala
        35                  40                  45

Ile Ile Gln Thr Leu Met Asn Ser Met Asp Pro Gly Ser Thr Pro Pro
    50                  55                  60

Ser Cys Cys Val Pro Thr Lys Leu Thr Pro Ile Ser Ile Leu Tyr Ile
65                  70                  75                  80

Asp Ala Gly Asn Asn Val Val Tyr Lys Gln Tyr Glu Asp Met Val Val
                85                  90                  95

Glu Ser Cys Gly Cys Arg
            100

<210> SEQ ID NO 6
<211> LENGTH: 102
<212> TYPE: PRT
<213> ORGANISM: Homo sapiens
<220> FEATURE:
<221> NAME/KEY: DOMAIN
<222> LOCATION: (1)..(102)
<223> OTHER INFORMATION: cystine-knot domain of GDF-7

<400> SEQUENCE: 6

Cys Ser Arg Lys Pro Leu His Val Asp Phe Lys Glu Leu Gly Trp Asp
1               5                   10                  15

Asp Trp Ile Ile Ala Pro Leu Asp Tyr Glu Ala Tyr His Cys Glu Gly
            20                  25                  30

Leu Cys Asp Phe Pro Leu Arg Ser His Leu Glu Pro Thr Asn His Ala
        35                  40                  45

Ile Ile Gln Thr Leu Leu Asn Ser Met Ala Pro Asp Ala Ala Pro Ala
    50                  55                  60

Ser Cys Cys Val Pro Ala Arg Leu Ser Pro Ile Ser Ile Leu Tyr Ile
65                  70                  75                  80

Asp Ala Ala Asn Asn Val Val Tyr Lys Gln Tyr Glu Asp Met Val Val
                85                  90                  95

Glu Ala Cys Gly Cys Arg
            100
```

GDF-5 MUTANT FOR INDUCING CARTILAGE FORMATION

PRIOR RELATED APPLICATIONS

This application is a National Phase application of International Application No. PCT/EP2012/074549, filed Dec. 5, 2012, which claims priority to European Patent Application No. 11191973.4, filed Dec. 5, 2011, each of which is incorporated herein by reference in its entirety.

The present invention is directed to GDF-5 related proteins having an improved capability of inducing cartilage formation and a reduced capability of inducing bone formation. The novel proteins are particularly useful in the treatment of cartilage defects, wherein the formation of bone tissue is undesirable.

Synovial joints are essential for the biomechanical function of the skeleton. An improper function as observed in arthritic diseases directly results in a severe loss of life quality. Therefore, joint biology has been in focus of extensive research for years leading to an understanding of joint anatomy and histology as well as the biomechanical properties and roles of articular cartilage and other components in joint function and maintenance.

GDF-5 (Hötten et al. 1994, Biochem. Biophys Res. Commun. 204, 646-652) is a morphogen which has been shown to promote cell proliferation, differentiation and/or tissue formation in several tissues. The protein is also known as morphogenic protein MP52, bone morphogenetic protein-14 (BMP-14) or cartilage-derived morphogenetic protein-1 (CDMP-1). GDF-5 shows chondrogenic activity and congenital GDF-5 mutations cause defects in digit, wrist and ankle joints in mice and humans (Storm et al., 1994; Thomas et al., 1997). The expression of GDF-5 is most strikingly limited to regions where joints will develop and is one of the earliest markers of joint formation (Storm and Kingsley, 1999). BMP receptor signaling is required for postnatal maintenance of articular cartilage (Rountree, 2004, PLoS Biol. 2004 November, 2(11))

GDF-5 is closely related to GDF-6 and GDF-7. These three proteins form a distinct subgroup of the TGF-β superfamily, thus displaying comparable biological properties and an extraordinary high degree of amino acid sequence identity (see i.e. Wolfman et al. 1997, J. Clin. Invest. 100, 321-330). All family members are initially synthesized as larger precursor proteins which subsequently undergo proteolytic cleavage at a cluster of basic residues approximately 110-140 amino acids from the C-terminus, thus releasing the C-terminal mature protein parts from the N-terminal prodomain. The mature polypeptides are structurally related and contain a conserved bioactive domain comprising six or seven canonical cysteine residues which is responsible for the characteristical three-dimensional "cystine-knot" motif of these proteins. Native GDF-5 related proteins are homodimeric molecules and act mainly through interaction with specific receptor complexes which are composed of type I and type II serine/threonine receptor kinases. The receptor kinases subsequently activate Smad proteins, which then propagate the signals into the nucleus to regulate target gene expression.

It has repeatedly been demonstrated that members of the GDF-5/-6/-7 subgroup are primarily important inducers and regulators of bone and cartilage (Cheng et al. 2003, J. Bone & Joint Surg. 85A, 1544-1552; Settle et al. 2003, Developm. Biol. 254, 116-130). GDF-5 and related proteins bind to and oligomerize two types of membrane bound serine-threonine kinase receptors termed type I and II. Upon ligand binding, these complexes transduce signals by phosphorylating members of the SMAD family of transcription factors, which upon activation enter the nucleus and regulate transcription of responsive genes (Massague, 1996). Recent experiments have implicated two different type I receptors in skeletal patterning, BMPR-IA and BMPR-IB. Both receptors are expressed in dynamic patterns during normal development. In several limb structures, for example, in joint interzones and perichondrium, an overlapping expression of BMPR-IA and BMPR-IB is observed (Mishina et al., 1995; Zou et al, 1997; Baur et al, 2000). With regard to the BMPR-IA and BMPR-IB expression patterns, GDF-5 signal transduction should be accomplished by the interaction with both BMPR-IA and BMPR-IB (Chang et al., 1994; Zou et al., 1997). Null mutations in the bmpr-1b gene produce viable mice with defects in bone and joint formation that closely resemble those seen in mice missing GDF-5 (Storm and Kingsley, 1996; Yi et al, 2000), whereas bmpr-la/mice are known to die early in embryogenesis (Mishina et al, 1995). However, a conditional knockout of BMPR-IA under the control of a GDF-5-Cre driver bypasses embryonic lethality and produces viable mice with normally formed joints. But, after birth articular cartilage within the joints wears away in a process reminiscent to osteoarthritis, which points at the importance of this receptor in cartilage homoeostasis and repair (Rountree et al., 2004).

The activity of the wild-type proteins of GDF-5 related protein family generally results in the formation of cartilage and bone. However, different medical conditions exist, wherein a formation of cartilage is desirable, however, the formation of bone tissue is undesired. For example, it is evident that in case of joint defects, the formation of cartilage is desirable whereas ossification should be avoided.

Therefore, the object of the present invention is to specifically use the effect of inducing cartilage formation of GDF-5 related proteins and to turn off the inducing effect of bone formation. Surprisingly, it was found out that it is possible to provide variants of GDF-5 related proteins having an improved capability of inducing cartilage formation and a reduced capability of inducing bone formation. This can be achieved by modifying GDF-5 related proteins such that they have an increased affinity for the BMPR-IB and/or a reduced affinity for the BMPR-IA.

Wild-type GDF-5 binds BMPR-IB in vitro with about 40- to 120-fold higher affinity ($K_D$~8-27 pM) as compared with BMPR-IA ($K_D$~1-1.1 nM). It was found that by modifying the binding affinity of GDF-5 related proteins such that the affinity for BMPR-IB is increased while the affinity for BMPR-IA is reduced, cartilage formation is facilitated while the formation of bone is reduced. This can be achieved by specific substitutions of one or more amino acid residues relating to a BMPR-IB and/or BMPR-IA binding site in the amino acid sequence of a GDF-5 related protein.

The binding affinity of GDF-5 related proteins having specific substitutions is compared to the binding affinity of human wild-type GDF-5 related protein, in particular human wild-type GDF-5.

In order to avoid misunderstandings and ambiguities, some frequently used terms herein are defined and exemplified as follows:

The term "cystine-knot domain" as used herein means the well known and conserved cysteine-rich amino acid region which is present in the mature parts of TGF-beta superfamily proteins such as i.e. human GDF-5 and forms a three-dimensional protein structure known as cystine-knot. In this domain the respective location of the cysteine residues to each other is important and is only allowed to vary slightly in order not to lose the biological activity. It has been demonstrated that the cystine-knot domain alone is sufficient for the biological function of the protein (Schreuder et al. (2005), Biochem Biophys Res Commun. 329, 1076-86). Consensus sequences for cystine-knot domains are well known in the state of the art. According to the definition defined herein the cystine-knot-domain of a protein starts with the first cysteine residue participating in the cystine-knot of the respective protein and ends with the residue which follows the last cysteine participating in the cystine-knot of the respective protein. For example, the cystine-knot domain of the human GDF-5 precursor protein (SEQ ID NO: 2) consists of the amino acids 400-501 (see also FIG. 1).

The term "GDF-5-related protein" as used herein means any naturally occurring or artificially created protein which is very closely related to human growth/differentiation factor 5 (hGDF-5). Common feature of all GFD-5-related proteins is the occurrence of a cystine-knot-domain with an amino acid identity of at least 60% to the 102 aa cystine-knot domain of human GDF-5 (amino acids 400-501 of SEQ ID NO: 2), which is sufficient for the biological function of the protein. The term "GDF-5-related proteins" includes proteins belonging to the group of GDF-5, GDF-6 and GDF-7 proteins from vertebrate or mammalian species as well as recombinant variants thereof as long as these proteins show the above mentioned percentage of identity with the cystine-knot domain of human GDF-5. The limiting value of 60% is well suitable to separate members of the GDF-5/-6/-7 group of proteins as well as variants thereof from further proteins such as more distantly related GDFs and BMPs. A comparison of the 102 as cystine-knot-domains of human GDF-5, human GDF-6 and human GDF-7 (see FIG. 2) reveals the high grade of amino acid identity between these proteins. Human GDF-6 shares 87 (85%) and human GDF-7 shares 83 (81%) identical residues with the cystine-knot-domain of human GDF-5. The respective domains of GDF-5/-6/-7 molecules from other vertebrate and mammalian species which have been identified so far also show very high identity percentages of at least 75% (between 79% and 99%), when compared with human GDF-5. In contrast, GDFs and BMPs not belonging to the GDF-5/-6/-7 subgroup display much lower identity values below 60%.

The determination of corresponding amino acid positions in related amino acid sequences as well as the calculation of percentages of identity can be easily performed with the help of well known alignment algorithms and optionally computer programs using these algorithms. For example, the amino acid identities in this patent application (i.e. FIG. 2) have been calculated by aligning sequences with the freeware program ClustalX (Version 1.81) with default parameters and subsequent counting of identical residues by hand. Default settings for pairwise alignment (slow-accurate) are: gap opening parameter: 10.00; gap extension parameter 0.10; Protein weight matrix: Gonnet 250. The ClustalX program is described in detail in Thompson, J. D., Gibson, T. J., Plewniak, F., Jeanmougin, F. and Higgins, D. G. (1997): The ClustalX windows interface: flexible strategies for multiple sequence alignment aided by quality analysis tools. Nucleic Acids Research 24:4876-4882. ClustalX is a windows interface for the ClustalW multiple sequence alignment program and is i.e. available from various sources, i.e. by anonymous ftp from ftp-igbmc.u-strasbg.fr, ftp.embl-heidelberg.de, ftp.ebi.ac.uk or via download from the following webpage: / world wide web-igbmc.u-strasbg.fr/Bio-Info/. The ClustalW program and algorithm is also described in detail in Thompson, J. D., Higgins, D. G. and Gibson, T. J. (1994): CLUSTALW: improving the sensitivity of progressive multiple sequence alignment through sequence weighting, positions-specific gap penalties and weight matrix choice. Nucleic Acids Research 22:4673-4680. Especially preferred GDF-5-related proteins display amino acid identities of at least 70%, 80%, 90% or 95% to the 102 aa cystine-knot domain of human GDF-5.

Non-limiting examples for vertebrate and mammalian GDF-5-related proteins are precursors and mature proteins of human GDF-5 (disclosed as MP52 in WO95/04819 and as human GDF-5 in Hotten et al. 1994, Biochem. Biophys Res. Commun. 204, 646-652), recombinant human (rh) GDF-5/MP52 (WO96/33215), MP52 Arg (WO97/06254); HMW human MP52s (WO97/04095), CDMP-1 (WO96/14335), mouse (*Mus musculus*) GDF-5 (U.S. Pat. No. 5,801,014), rabbit (*Oryctolagus cuniculus*) GDF-5 (Sanyal et al. 2000, Mol Biotechnol. 16, 203-210), chicken (*Gallus gallus*) GDF-5 (NCBI accession no. NP_989669), african clawed frog (*Xenopus laevis*) GDF-5 (NCBI accession no. AAT99303), monomeric GDF-5 (WO 01/11041 and WO 99/61611), human GDF-6/BMP-13 (U.S. Pat. No. 5,658,882), mouse GDF-6 (NCBI accession no NP_038554), GDF-6/CDMP-2 (WO96/14335), human GDF-7/BMP-12 (U.S. Pat. No. 5,658,882), mouse GDF-7 (NCBI accession no AAP97721), GDF-7/CDMP-3 (WO96/143335). Covered by the invention are also GDF-5-related proteins having additional mutations such as substitutions, additions and deletions, as long as these additional mutations do not completely abolish the biological protein activity.

The present invention is based on the finding of the inventors that it is possible by specific modifications in the region of the amino acid sequence of a GDF-5 related protein which is involved in the binding to BMPR-IB and/or BMPR-IA to change the protein in such a way that same has an improved ability of inducing cartilage formation and a reduced ability for inducing bone formation.

It was found out that proteins having an increased affinity for BMPR-IB and/or proteins having a reduced affinity for BMPR-IA are better capable for inducing cartilage formation while the formation of bone is reduced. These properties are especially pronounced in proteins showing both an increased affinity for BMPR-IB and a reduced affinity for BMPR-IA.

The GDF-5 related proteins of the present invention can be obtained by chemical modification or genetic engineering technology with recombinant proteins being preferred. The proteins can be obtained by replacing at least one amino acid residue relating to a BMPR-IB and/or BMPR-IA binding site in the amino acid sequence of a GDF-5 related protein. In particular, a substitution of one, two, three or more amino acid residues relating to a BMPR-IB binding site and/or a BMPR-IA binding site in the amino acid sequence of a GDF-5 related protein is preferred.

The above modification may be introduced in any known GDF-5 related proteins as defined above. Regarding the aspect of a therapeutic use of the protein, it is preferred to derive the protein from a human GDF-5 related protein, e.g from a human wild-type GDF-5 related protein such as GDF-5, GDF-6 or GDF-7. However, the proteins of the invention can also be derived from GDF-5 related proteins having additional mutations such as substitutions, additions or deletions as long as these additional mutations do not completely abolish the biological protein activity.

The GDF-5 related proteins as defined herein comprise a cystine-knot domain with an amino acid identity of at least 60%, preferably at least 75%, more preferably at least 80%, more preferably at least 90% and most preferably at least 95% to the 102 as cystine-knot domain of human GDF-5.

The GDF-5 related proteins of the present invention preferably comprise a substitution of one or more amino acids compared to the wild-type in the region which is involved in the binding to BMPR-IB and/or in the region which is involved in the binding to BMPR-IA. The regions of GDF-5 related proteins which are involved in binding to BMPR-IA and/or BMPR-IB are well known in the art or can easily be determined using methods that are within common knowledge.

Referring to the full-length amino acid sequence of the GDF-5 wild type, it is particularly preferred to replace one or more of the following amino acids (one letter code) by any different amino acid:

R 399;
any one of F 409 to W 417, preferably M 412, G 413, W 414, and/or W 417;
any one of E 434 to M 456, preferably F 435, P 436, L 437, R 438, S 439, H 440, P 443, N 445, V 448, I 449, L 452, M 453, S 455, and/or M 456;
S 475;
I 476;
F 478;
any one of K 488 to M 493, preferably K 488, Y 490, and/or D 492.

Preferably, the amino acid R 399 is replaced by V, L, I, M, F, Y, W, E or D.

Preferably, the amino acid M 412 is replaced by V, L, I, F, Y, W, H, K or R.

Preferably, the amino acid W 414 is replaced by R, K, F, Y, H, E or D.

Preferably, the amino acid W 417 is replaced by R, K, F, Y, H, E or D.

Preferably, the amino acid F 435 is replaced by V, L, I, M, P, Y, W, H, K or R. Preferably, the amino acid P 436 is replaced by V, L, I, M, F, Y or W.

Preferably, the amino acid L 437 is replaced by D or E.

Preferably, the amino acid R 438 is replaced by K, D, H, N, M, E, Q, S, T, Y or W.

Preferably, the amino acid S 439 is replaced by K, D, E, H, R, M, T, N, Q, Y or W.

Preferably, the amino acid H 440 is replaced by V, I, M, F, Y, W, E or D.

Preferably, the amino acid P 443 is replaced by V, L, I, M, F, Y, W, A or S.

Preferably, the amino acid N 445 is replaced by D, Q, H, F, L, R, K, M, S, Y or W.

Preferably, the amino acid V 448 is replaced by F, L, I, M, P, Y or W.

Preferably, the amino acid I 449 is replaced by F, L, V, M, P, Y or W.

Preferably, the amino acid L 452 is replaced by F, I, V, M, P, Y or W.

Preferably, the amino acid M 456 is replaced by F, I, L, P, Y, W, S, T, N, Q, K or D.

Preferably, the amino acid S 475 is replaced by M, T, N, Q, Y or W.

Preferably, the amino acid K 488 is replaced by R, M, S, T, N, Q, Y or W.

Preferably, the amino acid Y 490 is replaced by E, H, K, R, Q, F, T, M, S, N, Q or W.

Preferably, the amino acid D 492 is replaced by G, E, M, S, T, N, Q, Y, W, H, K or R.

Preferably, the amino acid I 476 is replaced by G, A, V, L, M, F, Y or W.

Preferably, the amino acid F 478 is replaced by G, A, V, L, I, Y or W.

The corresponding positions in the amino acid sequence of different GDF-5 related proteins can easily be derived from the above information regarding wild type GDF-5.

According to a first embodiment, at least one hydrophobic amino acid in the BMPR-IB and/or BMPR-IA binding site of a GDF-5 related protein is replaced with a hydrophilic or polar amino acid. Examples of hydrophilic or polar amino acid residues are aspartic acid, glutamic acid, lysine, arginine, histidine, serine and threonine.

According to a second embodiment, at least one hydrophilic or polar amino acid in the BMPR-IB and/or BMPR-IA binding site of a GDF-5 related protein is replaced with a hydrophobic amino acid. Examples of hydrophobic amino acids are alanine, isoleucine, leucine, methionine, phenylalanine, proline, tryptophan, tyrosine and valine.

According to another preferred embodiment, the protein of the present invention comprises a conservative substitution of at least one amino acid in the BMPR-IB and/or BMPR-IA binding site of a GDF-5 related protein. This means that the character of the amino acid which was originally present is kept. Accordingly, a hydrophilic or polar amino acid is replaced by another hydrophilic or polar amino acid or a hydrophobic amino acid is replaced by another hydrophobic amino acid.

Preferably, the conservative substitution is selected in such a way that an amino acid is exchanged by another amino acid having a different steric demand. According to this aspect of the invention, a hydrophobic amino acid can be replaced by a smaller or larger hydrophobic amino acid or a hydrophilic or polar amino acid can be replaced by a smaller or larger hydrophilic or polar amino acid.

The amino acid substitutions in the GDF-5 related proteins can be divided into 4 groups by means of the amino acid character:

I. Basic amino acid residues (R, K, H), replaced by
a) hydrophobic (V, L, I, M, P, F, Y, W)
b) acidic (E, D)
c) basic amino acid residues which are not identical to I. (R, K, H)
d) polar (S, T, N, Q).

II. Acidic amino acid residues (D), replaced by
a) hydrophobic (M, Y, W, G)
b) acidic (E)
c) basic (R, K, H)
d) polar (S, T, N, Q).

III. Hydrophobic amino acid residues (M, V, L, I, P, F, Y, W, A), replaced by
a) hydrophobic amino acid residues which are not identical to III. (M, V, L, I, P, F, Y, W, G, A)
b) acidic (E, D)
c) basic (R, K, H)
d) polar (S, T, N, Q)
d) small (A).

IV. Polar amino acid residues (S, T, N), replaced by
a) hydrophobic (M, V, L, I, P, F, Y, W)
b) acidic (E, D)
c) basic (R, K, H)
d) polar amino acid residues which are not identical to IV. (S, T, N, Q).

In a preferred embodiment, the GDF-5 related protein of the present invention comprises a sequence which matches one of the following amino acid sequences:

a)
ZCX$_1$X$_2$KX$_3$LHVX$_4$ZZZZZZZZZX$_7$IAPLX$_8$YEAX$_9$HCX$_{10}$GX$_{11}$CZZZZZ

ZZZZZZZZZZZZZZZZZZX$_{13}$PX$_{14}$X$_{15}$X$_{16}$PX$_{17}$X$_{18}$CCVPX$_{19}$X$_{20}$LX$_{21}$PI

ZILX$_{22}$X$_{23}$DX$_{24}$X$_{25}$NNVVYZZZZZZVVEX$_{27}$CGCR
or b)
ZCX$_1$X$_2$KX$_3$LHVX$_4$FX$_5$X$_6$ZZZDDZX$_7$IAPLX$_8$YEAX$_9$HCX$_{10}$GX$_{11}$CX$_{12}$ZZZ

ZZZLEZTZHAZZQTZZNZZX$_{13}$PX$_{14}$X$_{15}$X$_{16}$PX$_{17}$X$_{18}$CCVPX$_{19}$X$_{20}$LX$_{21}$PI

ZILX$_{22}$X$_{23}$DX$_{24}$X$_{25}$NNVVYZX$_{26}$ZZZMVVEX$_{27}$CGCR and wherein every X denotes any amino acid, every Z denotes any amino acid.

These generic sequences have been compiled from a comparison of the cystine-knot domains of vertebrate GDF-5, GDF-6 and GDF-7 sequences. Positions which are not conserved in the aligned proteins are denoted with an X in the generic sequences. Positions which are mutated according to the present invention are denoted with a Z.

In a more preferred embodiment, the GDF-5 related protein of the invention comprises a sequence which matches one of the above-mentioned generic amino acid sequences and wherein X$_1$ denotes asparagine (N) or serine (S)

X$_2$ denotes arginine (R) or lysine (K)

X$_3$ denotes alanine (A), glutamine (Q), proline (P) or serine (S)

X$_4$ denotes arginine (R) or lysine (K)

X$_5$ denotes aspartic acid (D) or glutamic acid (E)

X$_6$ denotes leucine (L) or methionine (M)

X$_7$ denotes isoleucine (I) or valine (V)

X$_8$ denotes aspartic acid (D) or glutamic acid (E)

X$_9$ denotes histidine (H), phenylalanine (F) or tyrosine (Y)

X$_{10}$ denotes aspartic acid (D) or glutamic acid (E)

X$_{11}$ denotes leucine (L)1 methionine (M) or valine (V)

X$_{12}$ denotes aspartic acid (D) or glutamic acid (E)

X$_{13}$ denotes alanine (A), asparagine (N) or aspartic acid (D)

X$_{14}$ denotes arginine (R), asparagine (N), aspartic acid (D), glutamic acid (E), glycine (G) or serine (S)

X$_{15}$ denotes alanine (A), asparagine (N), serine (S) or threonine (T)

X$_{16}$ denotes alanine (A), methionine (M) or threonine (T)

X$_{17}$ denotes alanine (A) or proline (P)

X$_{18}$ denotes serine (S) or threonine (T)

X$_{19}$ denotes alanine (A), serine (S) or threonine (T)

X$_{20}$ denotes arginine (R) or lysine (K)

X$_{21}$ denotes serine (S) or threonine (T)

X$_{22}$ denotes phenylalanine (F) or tyrosine (Y)

X$_{23}$ denotes isoleucine (I) or threonine (T)

X$_{24}$ denotes alanine (A) or serine (S)

X$_{25}$ denotes alanine (A) or glyine (G)

X$_{26}$ denotes glutamic acid (E) or glutamine (Q)

X$_{27}$ denotes alanine (A), glutamine (Q), serine (S) or threonine (T) and every Z denotes any amino acid.

In a particular embodiment, the GDF-5 related protein of the invention is derived from wild type GDF-5. According to this particular aspect, the GDF-5 related protein comprises a sequence which matches one of the following generic amino acid sequences a)
ZCSRKALHVNZZZZZZZZZIIAPLEYEAFHCEGLCZZZZZZZZZZZZZZ

ZZZZZZZZZDPESTPPTCCVPTRLSPIZILFIDSANNVVYZZZZZZVVE

SCGCR b)
ZCSRKALHVNFKDZZZDDZIIAPLEYEAFHCEGLCEZZZZZZLEZTZHA

ZZQTZZNZZDPESTPPTCCVPTRLSPIZILFIDSANNVVYZQZZZMVVE

SCGCR, wherein every Z denotes any amino acid.

An example for a protein as described above is a variant of human GDF-5, whereby the tryptophan residue at position 414 is exchanged against arginine (W414R). Referring to the mature sequence of GDF-5 (SEQ ID NO:4), this corresponds to a substitution at position 33. Surprisingly, it was found that this protein variant has a considerably reduced affinity for the BMPR-IA. In contrast, the affinity for the BMPR-IB is almost unaffected. Also preferred are other variants of GDF-5 related proteins comprising different amino acid substitutions than W414R.

An example for said variants of GDF-5 related proteins is a variant of human GDF-5, whereby the isoleucine residue at position 449 is exchanged against valine (I449V). Referring to the mature sequence of GDF-5 (SEQ ID NO: 4), this corresponds to a substitution at position 68. Said protein variant has reduced affinity for the BMPR-IA and an increased affinity for the BMPR-IB.

A further exemplary variant of GDF-5 related proteins comprises the amino acid substitution R399E. Referring to the mature sequence of GDF-5 (SEQ ID NO: 4), this corresponds to a substitution at position 18. Said protein variant has a reduced affinity for the BMPR-IA.

A still further exemplary variant of human GDF-5 is the variant, whereby the serine residue at position 439 is exchanged to glutamic acid (S439E). Referring to the mature sequence of GDF-5 (SEQ ID NO: 4), this corresponds to a substitution at position 58. Said protein variant also has a reduced affinity for the BMPR-IA.

Another exemplary variant of human GDF-5 is the variant, whereby the arginine residue at position 399 is exchanged to methionine (R399M). Referring to the mature sequence of GDF-5 (SEQ ID NO: 4), this corresponds to a substitution at position 18. Said protein variant has a considerably increased affinity for the BMPR-IB.

Preferably, the GDF-5 related proteins of the present invention are present as "isolated" proteins. This means that the protein of the present invention is substantially separated from other proteins and peptide molecules which are present in the natural source of the isolated protein (e.g. other polypeptides of the protein of the natural source). For example, a recombinant expressed peptide is considered isolated. According to a preferred embodiment of the invention, the GDF-5 related protein is a recombinant protein. Further, a peptide is also considered isolated, if it has been altered by human intervention or expressed by an organism that is not its natural source. Moreover, an "isolated" protein is free from some of the other cellular material with which it is naturally associated or cell culture medium, when produced by recombinant techniques or chemical precursors or other chemicals when chemically synthesized. Specifically excluded from the definition of "isolated" protein, are unpurified mixtures or compositions.

According to another embodiment, the present invention relates to a nucleic acid encoding a protein of the present invention. The nucleic acid has a sequence such that a substitution of one or more amino acid residues relating to a BMPR-IB and/or BMPR-IA binding site of the respective wild-type GDF-5 related protein is achieved. The base triplets coding for these amino acids and the degeneracy of the genetic code are generally known. The nucleic acid can be a DNA-sequence and/or a RNA-sequence as long as the protein according to the invention can be obtained from this nucleic acid upon expression in a suitable system. The nucleic acid of the invention may be wholly or partially synthetic. The nucleic acids comprise single stranded and/or wholly or partially double stranded polynucleotide sequences. The nucleic acid may be produced by any means including genomic preparations, cDNA preparations, in vitro synthesis, PCR, RT-PCR and/or in vitro or in vivo transcription.

Particularly preferred are "isolated" nucleic acids, which are substantially separated from nucleic acid molecules which are present in the natural source of the nucleic acid (e.g. sequences encoding other polypeptides). Preferably, an "isolated" nucleic acid is free of at least some of the sequences which naturally flank the nucleic acid (i.e. sequences located at the 5' and 3' ends of the nucleic acid) in its naturally occurring replicon. For example, a cloned nucleic acid is considered isolated. A nucleic acid is also considered isolated, if it has been altered by human intervention or placed in a locus or location that is not its natural site or if it is introduced into a cell. Moreover, an isolated nucleic acid can be free from some of the other cellular material with which it is naturally associated or culture medium when produced by recombinant techniques or chemical precursors or other chemicals when chemically synthesized.

In a preferred way, the nucleic acids of the invention can be prepared by a total gene synthesis or by site-directed mutagenesis of the nucleic acid encoding wild-type or modified GDF-5 related proteins. Methods include template directed ligation, recursive PCR, cassette mutagenesis, site directed mutagenesis or other techniques that are well-known in the art may be utilized.

The nucleic acids of the present invention may comprise further nucleic acid sequences which may add further functions to the isolated nucleic acid of the invention. For example, such additional nucleic acid sequences may comprise nucleic acid sequences that allow for proper expression of a protein of the invention and may encompass promoter sequences, regulatory sequences, stop signals, replication origins and like. The skilled person is well aware of such functional nucleic acid sequences and of how to arrange them in order to arrive at a nucleic acid molecule with the desired properties.

Expression vectors are a further subject matter of the present invention, wherein the nucleic acid is inserted in a suitable vector system, the vector system being selected according to the desired expression of the protein. The vector system can be a eukaryotic vector system but preferably is a prokaryotic vector system with which the proteins can be produced in a particularly easy and pure manner. A suitable expression vector is for example shown in WO 96/33215. The expression vector can also be a viral vector which can be used for example in gene therapy approaches.

Host cells and transgenic organisms are also a subject matter of the present invention. The host cells and transgenic organisms are characterized in that they contain a nucleic acid or an expression vector according to the invention and that they are able to use the information present in the nucleic acids and in the expression vector, respectively for the expression of the proteins according to the invention. Thus, the present invention relates to transgenic organisms or cells transiently or stably transformed or transfected with at least one nucleic acid or at least one vector encoding a protein of the invention or to a progeny of such transgenic organisms or cells. Furthermore, the present invention relates to cells, cell cultures, tissues and/or parts of transgenic organisms of the invention. It is understood that for the purpose of the present invention the term "transgenic organism" not only encompasses the organism where the nucleic acid of the invention has been transiently or stably introduced but also refers to the progeny of such organisms irrespective of the generation distance, provided that these organisms still comprise the nucleic acid of the invention and express the protein of the invention.

Preferably, the transgenic organism or cell is of prokaryotic or eukaryotic origin. Preferably, the transgenic organism is a microorganism. Preferred microorganisms are bacteria, yeasts, algae or fungi. Suitable host cells are preferably prokaryotic cells, in particular E. coli strains. Particularly useful host cells are defendants of E. coli W3110 as shown for example in WO 96/33215. In a preferred embodiment, host cells, preferably of human origin, may also be useful for a transplantation to patients in need thereof.

The preparation of a transformed organism or of a transformed cell requires introducing the appropriate DNA into the appropriate host organism or cell. A multiplicity of methods is available for this process which is referred to as transformation. Thus, by way of example, the DNA may be introduced directly by microinjection or by bombardment with DNA coated microparticles or nanoparticles. The cell may also be permeabilized chemically, for example using polyethylene glycol, so that the DNA can enter the cell via diffusion. The DNA may also be transformed via protoplast fusion with other DNA-containing units such as minicells, cells, lysosomes or liposomes. Another suitable method for introducing DNA is electroporation in which the cells are reversibly permeabilized by an electric impulse.

Another subject matter of the present invention is a method for producing a protein having an improved capability of inducing cartilage formation and a reduced capability of inducing bone formation, comprising the steps of:
(i) randomizing at least one amino acid position in a region of a GDF-5 related protein relating to a BMPR-IB and/or BMPR-IA binding site in order to obtain protein variants,
(ii) analyzing the protein variants obtained in (i) with respect to their affinity to the BMPR-IB and/or BMPR-IA,
(iii) selecting those protein variants which provide an increased affinity for the BMPR-IB and/or a reduced affinity for the BMPR-IA.

The regions of a GDF-5 related protein involved in binding to BMPR-IA or BMPR-IB are known in the art. In step (i) at least one amino acid position in one or both of these regions is randomized. It is preferred to randomize at least two, three or more amino acid positions. The amino acids present in the wild-type sequence of a GDF-5 related protein are replaced by other amino acids by chemical modifications or preferably by genetical engineering technology. Methods for producing the randomized protein variants of step (i) encompass the synthetic de novo synthesis of the proteins and/or the expression of the proteins from a nucleic acid encoding therefore. In a particular preferred way, the protein variants of step (i) are prepared by expression using the respective nucleic acids.

Preferably, protein variants are obtained for all other possible amino acids at the relevant position. However, it is also possible to carry out only a specific replacement of one or more amino acids against other amino acids. For example, hydrophilic amino acids can be replaced by hydrophobic amino acids. Alternatively, hydrophobic amino acids can be replaced by hydrophilic amino acids. A conservative substitution, wherein the hydrophilic or hydrophobic character is kept, is also possible. By the substitution, preferably an exchange against an amino acid having another steric demand is carried out.

The plurality of protein variants obtained in step (i) is then analyzed with respect to their affinity to BMPR-IB and/or to BMPR-IA. This can be effected in a way which is known and usual in the technical field. Methods for assessing protein-receptor interactions are common practice.

In step (iii), those protein variants which provide an increased affinity for BMPR-IB and/or a reduced affinity for BMPR-IA are selected. It was surprisingly found that these particular proteins have an improved capability of inducing cartilage formation and a reduced capability of inducing bone formation.

Another subject matter of the present invention concerns antibodies against the GDF-5 related proteins of the invention. These antibodies are specific for the claimed recombinant GDF-5 related proteins. Preferably, they are specific for the regions of GDF-5 related proteins containing one or more of the amino acid replacements described herein. Preferably, the antibodies are specific for a region of a recombinant protein derived from a GDF-5 related protein relating to a BMPR-IB and/or BMPR-IA binding site. These antibodies according to the present invention can be generated by using those fragments of the proteins of the invention as described above as immunogens to generate antibodies by known methods. The antibodies can be monoclonal or polyclonal and they can be any isotypes. Also comprised are antibody fragments such as Fab fragments or $Fab_2$ fragments. The antibodies can also be humanized antibodies or generic antibodies etc.

The antibodies of the present invention are, inter alia, suitable as an analytic tool. They can be used for investigating the absorption and distribution of a protein according to the invention in the body. Furthermore, the above antibodies are suitable for studying release kinetics.

Further subject matter of the present application is a pharmaceutical composition comprising the recombinant GDF-5 related protein or a nucleic acid or a vector or a host cell according to the invention. In principle, any pharmaceutical compositions which have already been published in context with GDF-5 related proteins are suitable. An expression vector or a host cell can be considered to be advantageous as active substances in a pharmaceutical composition. Also combinations of a protein according to the invention with other proteins can be used in preferred pharmaceutical compositions. Of course, the invention also comprises pharmaceutical compositions containing further substances like e.g. pharmacologically acceptable additives or carriers. The formulation may include antioxidants, preservatives, colouring, flavouring and emulsifying agents, suspending agents, solvents, fillers, bulking agents, buffers, delivery vehicles, excipients and/or pharmaceutical adjuvants. For example, a suitable carrier or vehicle may be water for injection, physiological saline solution or a saline solution mixed with a suitable carrier protein such as serum albumin. A preferred antioxidant for the preparation of the composition of the present invention is ascorbic acid.

The solvent or diluent of the pharmaceutical composition may be either aqueous or non-aqueous and may contain other pharmaceutically acceptable excipients which are capable of modifying and/or maintaining a pH, osmolarity, viscosity, clarity, scale, sterility, stability, rate of dissolution or odour of the formulation. Similarly other components may be included in the pharmaceutical composition according to the present invention in order to modify and/or maintain the rate of release of the pharmaceutically effective substance. Such modifying components are substances usually employed in the art in order to formulate dosages for parenteral administration in either unit or multi-dose form.

The finally formulated pharmaceutical composition prepared according to the present invention may be stored in sterile vials in form of a solution, suspension, gel, emulsion, solid or dehydrated or lyophilized powder. These formulations may be stored either in a ready-to-use form or in a form, e.g. in case of a lyophilized powder, which requires reconstitution prior to administration. The above and further suitable pharmaceutical formulations are known in the art and are described in, for example, Gus Remington's Pharmaceutical Sciences (18th Ed., Mack Publishing Co., Eastern, Pa., 1990, 1435-1712). Such formulations may influence the physical state, stability, rate of in vivo release and rate of in vivo clearance of the pharmaceutically effective component.

Other effective administration forms comprise parenteral slow-release, i.e. retarded, formulations, inhalent mists, or orally active formulations. For example, a slow-release formulation may comprise proteins bound to or incorporated into particulate preparations of polymeric compounds (such as polylactic acid, polyglycolic acid, etc.) or liposomes.

The pharmaceutical composition according to the present invention may also be formulated for parenteral administration, e.g., by infusion or injection, and may also include slow-release or sustained circulation formulations. Such parenterally administered therapeutic compositions are typically in the form of pyrogen-free, parenterally acceptable aqueous solutions comprising the pharmaceutically effective component(s) in a pharmaceutically acceptable carrier and/or diluent.

The pharmaceutical composition may comprise a matrix material, e.g. in cases where regeneration of cartilage is intended. It is advantageous to the protein, the nucleic acid, the expression vector or the host cell when they are applied in and/or on a biocompatible matrix material. Matrix material as used herein means a carrier or matrix acting as a scaffold for cell recruitment, attachment, proliferation and differentiation and/or as a potential delivery and storage device for the recombinant GDF-5 related proteins of the invention. In contrast to the solid matrices, carriers consist of amorphous materials having no defined surfaces and lacking a specific shape, i.e. alkyl cellulose, pluronics, gelatins, polyethylene glycols, dextrins, vegetable oils, sugars and other liquid and viscous substances.

Exemplary matrix materials are for example described in WO 98/21972. These matrix materials are equally suitable for the proteins according to the invention. The matrix material can be transplanted into the patient, e.g. surgically, wherein the protein or the DNA encoding the protein can be slowly released from the matrix material and then be effective over a long period of time. All types of matrix materials are useful in accordance with the present invention as long as they are biocompatible and selected for the intended area or indication of use. The matrix material can be a natural material, a modified natural material as well as a synthetic material. All already known matrices for morphogenetic proteins are encompassed. The extracellular matrix comprises for examples various collagens as for example types I, II, V, IX, X, XI and XIII, further proteoglycans and glycosamino glycans as for example chondroitin sulfates, biglycans, decorines and/or hyaluronic acid or non-collageneous proteins as e.g. osteopontin, laminin, fibronectin, vitronectin and cartilage matrix protein. All mentioned natural materials may also be used in artificially modified forms. For a non-limiting list of useful carriers and matrices (see further Kirker-Head, 2000, Advanced Drug Delivery 43, 65-92).

A further subject-matter of the present invention concerns liposomal formulations comprising the recombinant GDF-5 related protein according to the invention. Liposomes used in said formulations are commonly known to the person skilled in the art. In particular, preferred liposomal formulations are disclosed in WO 2008/049588. More preferred liposomal formulations are described on pages 9 to 13 of WO 2008/049588.

Furthermore, the GDF-5 related proteins of the invention can be administered in combination with other pharmaceutically active substances. Said pharmaceutically active substances can be, for example, painkillers such as locally effective painkillers or other substances that have a positive effect on diseases, wherein the formation of cartilage is desired, like protease inhibitors. These are only examples of possible additives, and a worker skilled in the art can easily add other excipients which are in use in pharmaceutical preparations or which are generally regarded as safe.

Due to their improved capability of inducing cartilage formation, the recombinant GDF-5 related proteins of the present invention are particularly suitable for use in the treatment of diseases, wherein the formation of cartilage is desired but the formation of bone is undesirable. Thus another aspect of the present invention is the use of the present proteins, nucleic acids, vectors or host cells in the treatment of these diseases. In particular, the present proteins, nucleic acids, vectors or host cells are for use in the treatment of cartilage defects or for the treatment of traumatic rupture or detachment of cartilage,
in particular age-related cartilage defects for example due to wear, osteoarthritis, rheumatoid arthritis, sports related injuries, diseases which can affect the cartilage like chondrodystrophies, diseases characterized by disturbance of growth and subsequent ossification of cartilage, achondroplasia, costochondritis, spinal disc herniation and spinal disc repair, relapsing polychondritis,
repair of cartilage defects associated with tumors, either benign or malignant, like chondroma or chondrosarcoma.

Another embodiment of the present invention is a method for the treatment of diseases, wherein the formation of cartilage is desired but the formation of bone is undesirable comprising the step of administering a protein, nucleic acid, vector or host cell according to the invention to a patient in need of such treatment.

As used herein, the term "treating" refers to reversing, alleviating or inhibiting the progress of a disease, disorder or condition or one or more symptoms of such disease, disorder or condition to which such term applies. As used herein, treating may also refer to decreasing the probability or incidence of the occurrence of a disease, disorder or condition in a mammal as compared to an untreated control population or as compared to the same mammal prior to treatment. For example, as used herein, treating may refer to preventing a disease, disorder or condition and may include delaying or preventing the onset of a disease, disorder or condition or delaying or preventing the symptoms associated with a disease, disorder or condition. As used herein, treating may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention as described herein to a subject that is not at the time of administration afflicted with the disease, disorder or condition. As used herein, treating may also refer to preventing the recurrence of a disease, disorder or condition or of one or more symptoms associated with such disease, disorder or condition.

The following Examples together with the Figures and Sequence Protocols are intended to further illustrate the invention.

SEQ ID NO: 1 shows the DNA sequence, and SEQ ID NO: 2 shows the protein sequence of the human GDF-5 precursor.

SEQ ID NO: 3 shows the DNA sequence and SEQ ID NO: 4 shows the protein sequence of the human mature monomeric GDF-5.

FIGURES

FIG. 1 shows additional features of the human GDF5-precursor protein according to SEQ ID NO: 2:
aa 001-381 of SEQ ID NO: 2 (pre-prodomain (bold letters))
aa 001-027 of SEQ ID NO: 2 (signal peptide (bold and underlined))
aa 382-501 of SEQ ID NO: 2 (mature protein part)
aa 400-501 of SEQ ID NO: 2 (cystine-knot domain (underlined))

FIG. 2 shows a comparison of the 102 aa cystine-knot domains of human GDF-5 (SEQ ID NO: 2), human GDF-6 (sequence 26 from U.S. Pat. No. 5,658,882)(SEQ ID NO: 5) and human GDF-7 (sequence 2 from U.S. Pat. No. 5,658,882) (SEQ ID NO: 6). Amino acid residues which are identical in all three molecules are highlighted by borders.

FIG. 8 shows the results of an alkaline phosphatase assay (ALP) with recombinant human GDF-5 mutant W414R (as described in example 3).

EXAMPLE 1

Figure 2:
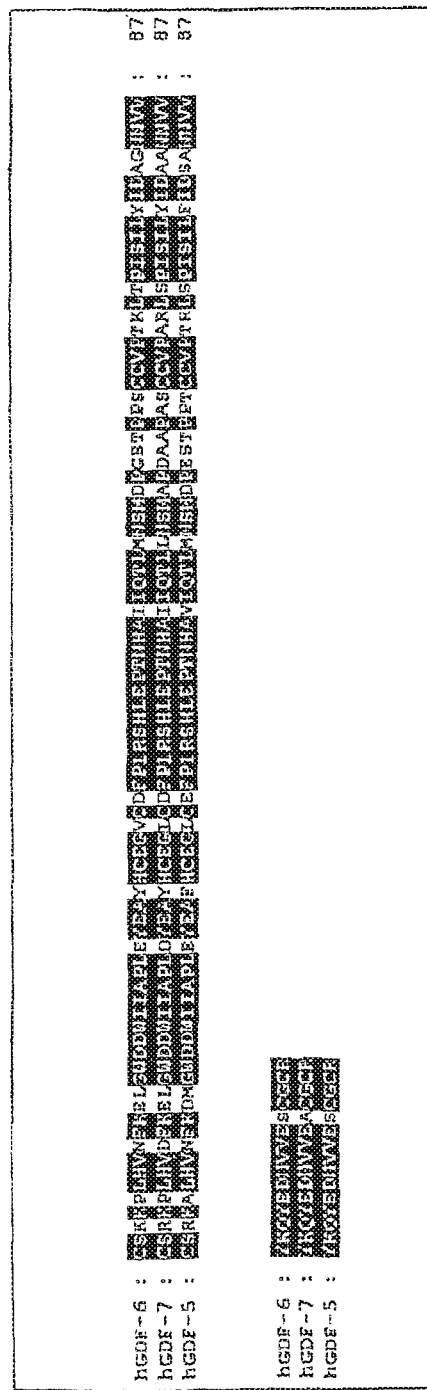

Creation, Expression and Purification of GDF-Related Proteins

DNAs coding for the mature parts of human GDF-5, human GDF-6 and human GDF-7 proteins have been isolated from human ROB-C26 osteoprogenitor cells (Yamaguchi et al. 1991, Calcif. Tissue Int. 49, 221-225) via RT-PCR technique and subsequently ligated into prokaryotic plasmid vectors. In order to identify functionally important amino acid residues in the mature parts of GDF-5, -6 and -7, various single mutations have been introduced into these sequences via site directed mutagenesis. All individual mutations were created by using the QuickChange™ site-directed mutagenesis kit with the PfuTurboTm DNA polymerase and the DPN I endonuclease from Stratagene according to the instruction manual of the manufacturer.

Using the bacterial strain W3110BP transformed with the plasmids and induced with IPTG, the proteins were expressed in inclusion bodies. These inclusion bodies were isolated using a homogenization buffer (25 mM Tris HCl pH 7.3, 10 mM EDTA NaOH pH 8, 8 M Urea) and wash buffer (1 M Urea, 20 mM Tris HCl, pH 8.3, 10 mM EDTA NaOH pH 8.0) according to standard procedures. Further purification was carried out on a reversed phase column Aquapore Octyl (Applied Biosys, (CV=7.8 ml) 100×10, 20µ, No 186470) with a gradient from 100% of Eluent A (0.1% TFA, HPLC $H_2O$) to 100% Eluent B (0.1% TFA, 90% $CH_3N$, HPLC $H_2O$) in 104 minutes (flow rate: 3 ml/min). After a western blot control, the fractions containing the mutant protein were pooled and lyophilized.

The mutant proteins were dissolved in dissolving buffer (6 M Guanidine HCl, 50 m M Tris, 150 mM NaCl, 3 mM DTT, pH=8.0), the protein concentration was exactly adjusted to 2.6 mg/ml and the pH was adjusted between 8 and 9. After 2 h incubation at room temperature, refolding buffer (1 M NaCl, 50 mM Tris, 5 mM EDTA, 1 mM GSSG, 2 mM GSH, 33 mM Chaps, pH=9.5) was added under gentle agitation to reach a final concentration of 0.16 mg/ml.

The solution was then incubated for 48 h at 22° C. and the refolding was stopped by changing the pH to 3-4 by adding 18% HCl. After centrifugation, the non-refolded monomer was separated from the dimer form by carrying out a second RP-HPLC under the same conditions. The fractions containing the dimerized protein were pooled, lyophilized and stored at −70° C.

EXAMPLE 2

Measurement of the Biological Activity of Different Variants of GDF-related Proteins In Vitro by ALP Assay $2.0 \times 10^5$ cells of C2C12-Ib (a cell line stably overexpressing the BMPR-IB receptor) and cells of C2C12 were incubated for 3-4 days in 20 ml cell culture medium (alpha-MEM, Penicillin/Streptomycin, 2 mM L-glutamine, 10% FCS) at 37° C., 5% $CO_2$, $H_2O$-saturated. The cells were subsequently washed with PBS (phosphate buffered saline), trypsinated and resuspended in culture medium to a density of $3 \times 10^4$ cells/ml. 150 µl were transferred to each well of a 96 well culture plate and incubated for 24 h at 37° C., 5% $CO_2$, $H_2O$-saturated. After washing with medium the wells were filled with 120 µl of new culture medium. 40 µl of different dilutions of mutant or wild type protein (dissolved in 10 mM HCl and diluted at least 250 fold in medium) were added, followed by another incubation step for 72 h at 37° C., 5% $CO_2$, $H_2O$-saturated. After washing with PBS, 150 µl of lysis solution (0.2% Nonidet P40, 0.2 g $MgCl_2 \times 6H_2O$, adjusted to 1000 ml with water) was added, followed by 15-18 h incubation at 37° C., 5% $CO_2$, $H_2O$-saturated. 50 µl of each well were subsequently transferred to a new 96 well plate. 50 µl of substrate solution (2.5× concentrated diethanolamine substrate buffer+148 g/l PNPP (sodium p-nitrophenyl-phosphate)) was then added to each well and the plates were incubated for 4 min at 37° C., 5% $CO_2$, $H_2O$-saturated. The ALP-reaction was stopped afterwards with 100 µl of 30 g/l NaOH and finally the optical density was measured with an automatic microplate reader at 405 nm under consideration of blank value subtraction.

Figure 3:
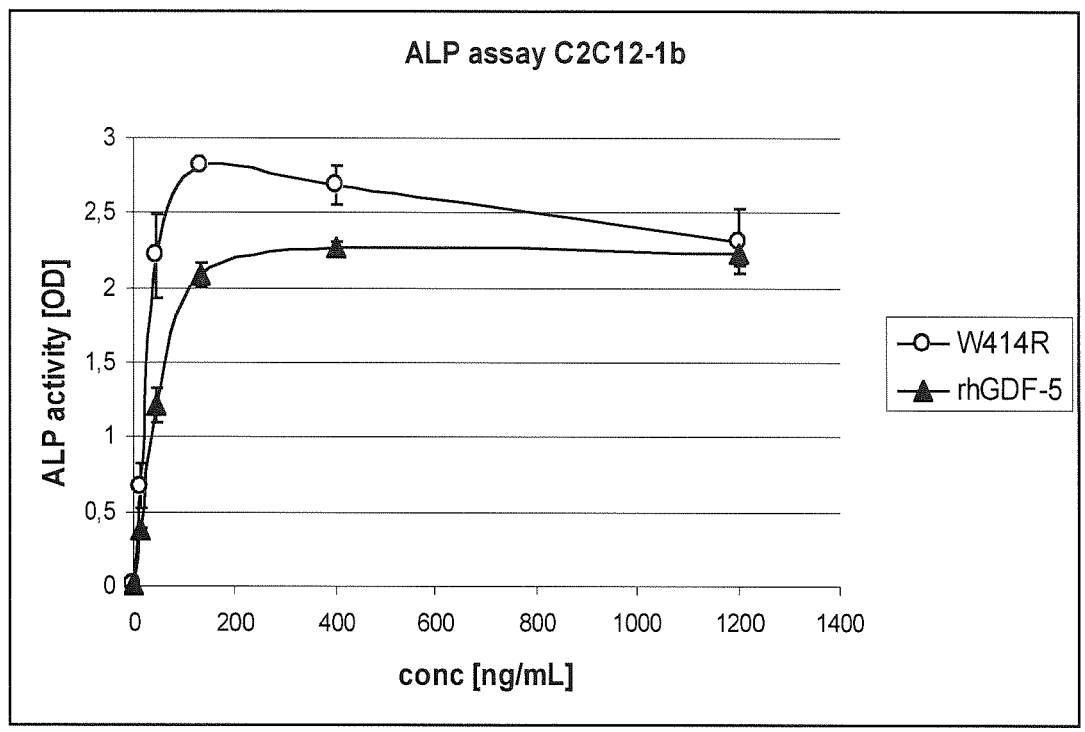
FIG. 3 shows the results of an alkaline phosphatase assay (ALP) with recombinant human GDF-5 mutant W414R (as described in example 2).
Figure 4:
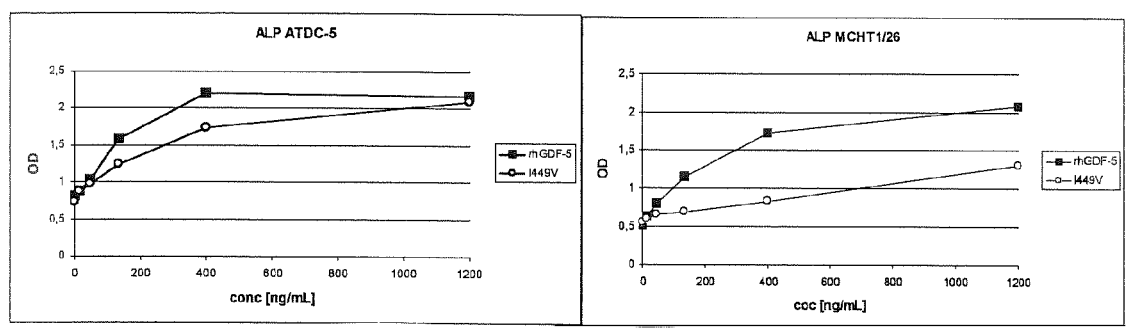
FIG. 4 shows the results of an alkaline phosphatase assay (ALP) with recombinant human GDF-5 mutant I449V (as described in example 3).
Figure 5:
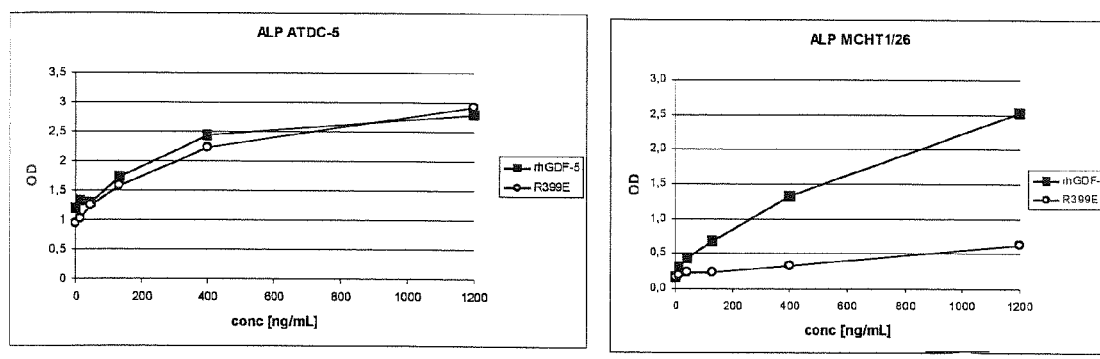
FIG. 5 shows the results of an alkaline phosphatase assay (ALP) with recombinant human GDF-5 mutant R399E (as described in example 3).
Figure 6:
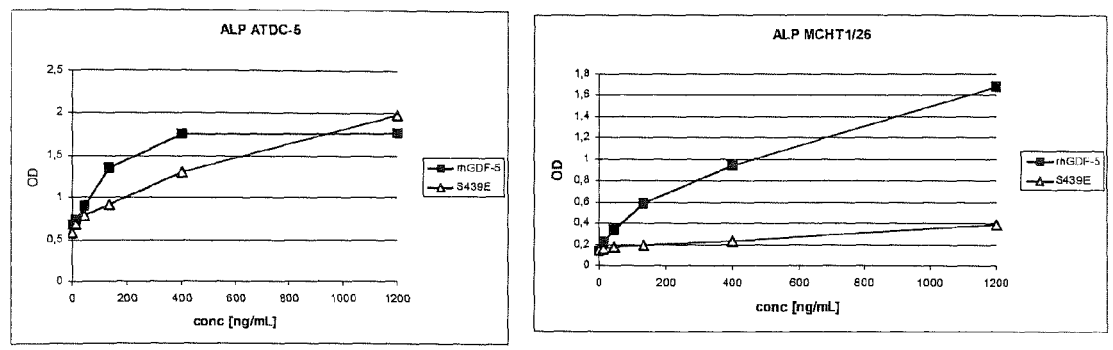
FIG. 6 shows the results of an alkaline phosphatase assay (ALP) with recombinant human GDF-5 mutant S439E (as described in example 3).
Figure 7:
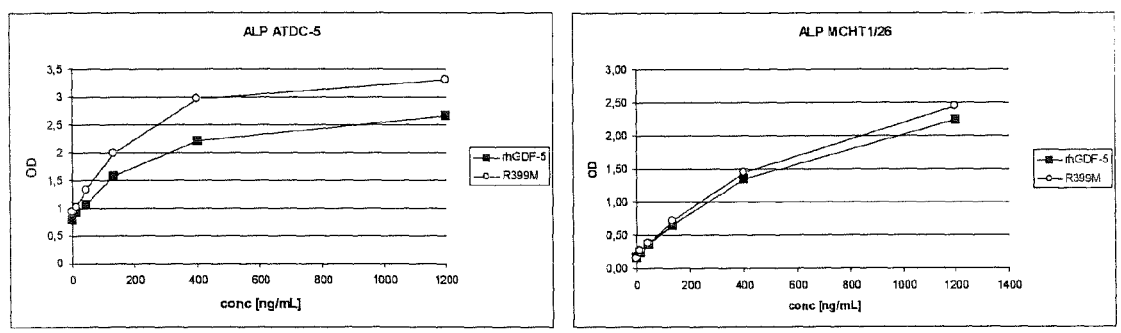
FIG. 7 shows the results of an alkaline phosphatase assay (ALP) with recombinant human GDF-5 mutant R399M (as described in example 3).

As an example, results (average values of 2 independent experiments) regarding hGDF-5 mutant W414R for C2C12-Ib cells are shown in FIG. 3. Five different protein concentrations (14 ng/mL, 44.5 ng/mL, 133.2 ng/mL, 400 ng/mL and 1200 ng/mL) have been used in this assay. The mutant protein W414R exhibits biological activity in cells where the BMPR-IB receptor (02012-Ib cells) is overexpressed, indicating that the BMPR-IB binding site of W414R is functional active. Wildtype protein (rhGDF-5) served as a control in the assay system.

Further results of the biological activity of further hGDF-5 mutants for the cell lines C2C12 and C2C12-Ib are shown in table 1.

EXAMPLE 3

Measurement of the Biological Activity of Different Variants of GDF-Related Proteins In Vitro by ALP Assay $5 \times 10^5$ cells of ATDC-5 cells and $5 \times 10^5$ cells for MCHT1/26 were incubated for 3-4 days in 20 ml cell culture medium (alpha-MEM, 2 mM L-glutamine, 10% FCS, for MCHT1/26; DMEM/F12 (1:1), 5% FCS) at 37° C., 5% $CO_2$, $H_2O$-saturated. The cells were subsequently washed with PBS (phosphate buffered saline), trypsinated and resuspended in culture medium to a density of $3 \times 10^4$ cells/ml. 150 µl were transferred to each well of a 96 well culture plate and incubated for 24 h at 37° C., 5% $CO_2$, $H_2O$-saturated. After washing with medium the wells were filled with 120 µl of new culture medium for MCHT1/26 and 120 µl assay medium for ATDC-5 (DMEM/F12 (1:1), 0.5% FCS) plus 40 µl of different dilutions of mutant or wild type protein (dissolved in 10 mM HCl and diluted at least 250 fold in medium) were added, followed by another incubation step for 72 h at 37° C., 5% $CO_2$, $H_2O$-saturated. After washing with PBS, 150 µl of lysis solution (MCHT1/26 lysis solution: 0.2% Nonidet P40, 1 mM $MgCl_2$, ATDC-5 lysis solution: 100 mM Na-Glycine, 1% Nonidet P40, 1 mM $MgCl_2$) was added, followed by 1 h incubation for ATDC-5 and 15-18 h for MCHT1/26 at 37° C., 5% $CO_2$, $H_2O$-saturated. 50 µl of each well were subsequently transferred to a new 96 well plate. 50 µl of substrate solution (2.5× concentrated diethanolamine substrate buffer+148 g/l PNPP (sodium p-nitrophenyl-phosphate)) was then added to each well and the plates were incubated for another 60 min at 37° C., 5% $CO_2$, $H_2O$-saturated. The ALP-reaction was stopped afterwards with 100 µl of 30 g/l NaOH and finally the optical density was measured with an automatic microplate reader at 405 nm under consideration of blank value subtraction.

Exemplary results (average values of 2 independent experiments) regarding the hGDF-5 mutants I449V, R399E, S439E, R399M, W414R are shown in FIG. 4-8, respectively. Five different protein concentrations (14.8 ng/ml, 44.5 ng/ml, 133.2 ng/ml, 400 ng/ml, 1200 ng/ml) have been used in this assay. Compared to wild-type GDF-5 the mutant proteins exhibit a higher biological activity on ATDC-5 cells compared to MCHT1/26 cells in this assay system.

EXAMPLE 4

Biacore Affinity Measurement of GDF-5-Related Proteins

A BiacoreT100 system (Biacore, GE Healthcare, Chalfont St. Giles, GB) was used for all biosensor experiments.

Approximately 200 resonance units (RU) of the Fc-fusion protein receptor ectodomains of BMPR-IB, BMPR-IA, or BMPR-II were immobilized to protein G CM5 biosensor chips. Interaction sensorgrams were recorded at a flow rate of 60 μl/min at 30° C. in 10 mM HEPES (pH 7.4), 300 mM NaCl, 3.4 mM EDTA, 0.005% Tween 20. The experiments were carried out in duplicate using ligand concentrations of 0.05 to 100 nM. All apparent binding affinities were obtained using BIAevaluation v. 2.2.4 (Biacore, GE Healthcare, Chalfont St. Giles, GB). The affinities for ligand type I receptor interaction were derived by fitting the kinetic data to a 1:1 Langmuir binding model (KD (kin)). Due to too fast binding kinetics (exceeding 106 M-1 s-1 (for kon) and 10-2 s-1 (for koff)) the apparent binding affinities for the ligand:BMPR-II interaction were determined from the dose dependency of equilibrium binding (KD (eq)).

The results of the Biacore affinity measurements for different variants of human GDF-5 are shown in table 1.

| | ALP | | | | Biacore (KD) | | | fold higher IB affinity over IA KD(IA): KD(IB) [M] | fold higher IB affinity over IA compared to WT |
|---|---|---|---|---|---|---|---|---|---|
| | MCHT1/26 | ATDC-5 | C2C12 | C2C12-Ib | BMPR-IA | BMPR-IB | BMPR-II | | |
| GDF 5 WT | +++ | +++ | 0 | +++ | 1*-1.1** nM | 8*-27** pM | 32 nM | 40**-122* | 1 |
| R399M | +++ | ++++ | + | ++ | 0.54 nM* | 2.5 pM* | 32 nM | 216* | 1.8 |
| R399E | 0 | +++ | 0 | ++ | 22.5 nM* | 172 pM* | 32 nM | 130* | 1.1 |
| M412V | 0 | ++ | 0 | ++ | 13 nM** | 39 pM** | n.d. | 333** | 8.3 |
| W414R | 0 | + | 0 | +++ | 20.3 nM* | 30 pM* | no binding | 668* | 5.5 |
| W417F | 0/+ | + | 0 | +++ | 27 nM** | 46 pM** | n.d. | 587** | 14.7 |
| W417R | 0 | + | 0 | +++ | 98 nM** | 37 pM** | n.d. | 2649** | 56.2 |
| R438K | + | ++ | 0 | ++(+) | 32.5 nM* | 45 pM* | 32 nM | 717* | 5.9 |
| S439K | 0 | + | 0 | ++ | 43.4 nM* | 10 pM* | 10 nM | 2400* | 19.7 |
| S439E | 0 | ++ | 0 | ++(+) | 25 nM** | 43 pM** | n.d. | 581** | 14.5 |
| I449V | 0/+ | + | 0 | +(+) | 5.7 nM** | 26 pM** | n.d. | 219** | 5.5 |

*= Results of affinity measurement 1 concerning GDF-5 wild type, affinity to BMPR-IA: 1 nM, affinity to BMPR-IB: 8 pM
**= Results of affinity measurement 2 concerning GDF-5 wild type, affinity to BMPR-IA: 1.1 nM, affinity to BMPR-IB: 27 pM
0 = No ALP activity
+ to +++++ = ALP activity, number + represents the intensity of the ALP activity
n.d. = not determined

The invention claimed is:

1. A GDF-5 related protein, having an improved capability of inducing cartilage formation or a reduced capability of inducing bone formation, wherein the protein has an increased affinity for the BMP receptor IB (BMPR-IB) and/or a reduced affinity for the BMP receptor IA (BMPR-IA) and wherein, referring to the full-length amino acid sequence of wild-type GDF 5 protein, one or more of the following amino acids, or one or more amino acids at corresponding positions in a different GDF-5 related protein are replaced by the specified amino acid:
R399 is replaced by M or E;
W414 is replaced by R;
W417 is replaced by R or F;
R438 is replaced by K;
S439 is replaced by K or E;
I449 is replaced by V.

2. The protein of claim 1, wherein the protein is obtained by replacing at least one amino acid residue relating to a BMPR-IB and/or a BMPR-IA binding site in the amino acid sequence of the GDF-5 related protein, preferably by genetic engineering technology.

3. The protein of claim 2, wherein the protein is derived from a human wild-type GDF-5 related protein, in particular from human GDF-5, GDF-6 or GDF-7.

4. The protein of claim 1, wherein at least one hydrophobic amino acid in the BMPR-IB and/or the BMPR-IA binding site of the GDF-5-related protein is replaced with a hydrophilic or polar amino acid.

5. The protein of claim 1, wherein at least one hydrophilic or polar amino acid in the BMPR-IB and/or the BMPR-IA binding site of the GDF-5 related protein is replaced with a hydrophobic amino acid.

6. The protein of claim 1, comprising a conservative substitution of at least one amino acid in the BMPR-IB and/or the BMPR-IA binding site of the GDF-5 related protein,
in particular wherein a hydrophobic amino acid is replaced by a smaller or larger hydrophobic amino acid or wherein a hydrophilic or polar amino acid is replaced by a smaller or lager hydrophilic or polar amino acid.

7. The protein of claim 1 for use in the treatment of diseases, wherein the formation of cartilage is desired but the formation of bone is undesirable.

8. The protein of claim 7 for use in the treatment of cartilage defects or for the treatment of traumatic rupture or detachment of cartilage,
in particular age-related cartilage defects for example due to wear, osteoarthritis, rheumatoid arthritis, sports related injuries,
diseases which can affect the cartilage like chondrodystrophies, diseases characterized by disturbance of growth and subsequent ossification of cartilage, achondroplasia, costochondritis, spinal disc herniation and spinal disc repair, relapsing polychondritis,
repair of cartilage defects associated with tumors, either benign or malignant, like chondroma or chondrosarcoma.

9. A pharmaceutical composition comprising the protein of claim 1, optionally in combination with pharmaceutically acceptable additives or carriers.

10. A GDF-5 related protein wherein referring to the full-length amino acid sequence of wild-type GDF-5 protein, R399 or an amino acid at the corresponding position in a different GDF-5 related protein, is replaced with E.

11. A GDF-5 related protein wherein, referring to the full-length amino acid sequence of wild-type GDF-5protein, W417 or an amino acid at the corresponding position in a different GDF-5 related protein, is replaced with F or R.

12. The GDF-5 related protein of claim 1, wherein the GDF-5 related protein is a mature GDF-5 related protein.

* * * * *

UNITED STATES PATENT AND TRADEMARK OFFICE
CERTIFICATE OF CORRECTION

PATENT NO. : 9,718,867 B2  
APPLICATION NO. : 14/362691  
DATED : August 1, 2017  
INVENTOR(S) : Frank Ploger and Florian Wagner Page 1 of 1

It is certified that error appears in the above-identified patent and that said Letters Patent is hereby corrected as shown below:

On the Title Page

Item (73), Assignee:
Please delete "BIOPHARMA GESELLSCHAFT ZUR BIOTECHNOLOGISCHEN ENTWICKLUNG VON PHARMAKA MBH"
And replace with -- BIOPHARM GESELLSCHAFT ZUR BIOTECHNOLOGISCHEN ENTWICKLUNG VON PHARMAKA MBH --

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*